United States Patent [19]
Berthoux et al.

[11] 4,096,150
[45] Jun. 20, 1978

[54] PROCESS FOR MANUFACTURE OF TERTIARY AMINES

[75] Inventors: Jean Berthoux; Yvonick Chevallier, both of Decines; Jacques-Pierre Martinaud, Lyons, all of France

[73] Assignee: Rhone-Progil, Courbevoie, France

[21] Appl. No.: 420,976

[22] Filed: Dec. 3, 1973

[30] Foreign Application Priority Data

Dec. 20, 1972  France .................................. 72.46270

[51] Int. Cl.² .............................................. C07D 211/02
[52] U.S. Cl. ............................... 260/293.52; 260/568; 260/570.9; 260/576; 260/583 R
[58] Field of Search ................ 260/293.52, 568, 570.9, 260/576, 583 R, 585 D

[56] References Cited

U.S. PATENT DOCUMENTS

| 2,422,631 | 6/1947 | Olin et al. | 260/583 |
| 2,497,310 | 2/1950 | Larson | 260/585 |
| 3,513,200 | 5/1970 | Biale | 260/583 |
| 3,758,586 | 9/1973 | Coulson | 260/583 R |

FOREIGN PATENT DOCUMENTS 1,395,489  5/1964  France.

*Primary Examiner*—Henry R. Jiles
*Assistant Examiner*—Richard A. Schwartz
*Attorney, Agent, or Firm*—Browdy & Neimark

[57] ABSTRACT

Substituted amines are prepared with high selectivity by reacting olefin, hydrogen, CO and secondary amine in the presence of a coordination complex catalyst of a Group VIII metal and a ligand, the donor atom of which is oxygen, nitrogen or sulfur.

8 Claims, No Drawings

PROCESS FOR MANUFACTURE OF TERTIARY AMINES

FIELD OF INVENTION

The present invention relates to the manufacture of substituted amines, and more particularly, to a process for the manufacture of substituted amines by reaction between olefins, hydrogen, carbon monoxide and secondary amines.

BACKGROUND

The principle of obtaining amines starting from an olefin, hydrogen, CO and a secondary amine is known. Various techniques embodying this principle have been described using catalysts of definite kinds. Thus, U.S. Pat. Nos. 2,422,631 and 2,497,310 recommend utilization of metals of Groups VI, VII and VIII, and so on, in the form of their salts or oxides. The reaction is carried on under a high pressure and leads to a moderate selectivity in amines. French Pat. No. 1,395,489 of May 25, 1964 claims the use of a complex of tri(hydrocarbyl) phosphine and cobalt carbonyl. The conversion rate of olefins into amines is about 50% at a pressure between 7 and 21 atmospheres and a temperature from 100° to 250° C.

U.S. Pat. No. 3,513,200 covers the utilization of complexes bearing a phosphine and, optionally, a metal of Group VIII hydride. There can be added, as an adjuvant, poly (heterocyclo) amines at least a nitrogen atom of which is common to 2 cycles of the polycyclic compound. The reaction is realized at a temperature between 50° and 200° C and under a pressure ranging from 5 to 300 atmospheres. A significant proportion of aldehydes is obtained and the selectivity in amines is still in this case only very moderate.

The various above-mentioned processes thus all lead to the formation of significant quantities of undesired by-products. This is confirmed in general treatises such as: "Carbon monoxide in organic synthesis", of Falbe. These by-products which are obtained in significant proportions are chiefly aldehydes, alcohols and amides, the aldehydes moreover being liable to condense on themselves under the reaction conditions. From this group of facts, the noted selectivity in amines is always only moderate and in some cases even mediocre, generally ranging between 20 and 50%.

SUMMARY

It has now been discovered that synthesis of substituted amines can be carried on without the above-mentioned drawbacks, by using the process according the present invention. It is, accordingly, an object of the present invention to overcome the defects of the prior art, such as indicated above. It is another object to provide for the improved preparation of substituted amines. It is another object to provide an improved process leading to better selectivity of the final substituted amines.

It has now been found that improved results are obtained by the use of a particular group of coordination complexes of Group VIII metals characterized in that they comprise at least one of the following ligands: phosphites or ligands, the "donor" atom of which is oxygen, sulfur or nitrogen. These constitute a group of catalysts permitting the olefin(s) to react with hydrogen, carbon monoxide and the amines, under a pressure from 30 to 200 bars, at a temperature from 60° to 250° C for a reaction time from 10 minutes to 10 hours, to thereby obtain a selectivity in substituted amines, which is always greater than 60% and which can reach 100%.

To the attainment of the above mentioned ends and the accomplishment of the above as well as other new and useful objects as will appear below, the present invention is described in greater detail by way of the following exemplary and non-limitative descriptions of certain embodiments.

DETAILED DESCRIPTION

The coordination complexes which constitute the catalysts of the present invention comprise the association of the following elements: (1) on the one hand a Group VIII metal such as rhodium, iridium, platinum, palladium, ruthenium, osmium, iron, cobalt or nickel; (2) on the other hand at least one of the following ligands: aliphatic, aromatic, arylaliphatic phosphites, and so on . . . ; hexamethylphosphorotriamide; aliphatic and cyclic ethers such as dimethyl and diethyl oxide, dioxane, glycol dialkylethers, acetylacetone and so on; primary, secondary, tertiary aliphatic, aromatic and alicyclic amines, heterocyclic bases, pyridine, bipyridine and so on; dialkyl and diaryl sulphides, alicyclic sulfides, sulfur-containing heterocycles and so on; ligands comprising several donor atoms such as dimethylsulfoxide, dimethylglyoxime, amine oxides and so on. In addition to these ligands which are absolutely necessary, there can also be present other ligands having a suitable and non-interferring nature.

The catalysts can be prepared either separately, and isolated according to known techniques or in situ without a previous isolation, by putting together a suitable precursor and the chosen ligand, optionally in excess. For instance, a carbonyl complex such as di $\mu$-chlorotetracarbonyl-di-Rhodium or an olefinic complex such as di $\mu$-chlorotetraethylene-di-Rhodium can be used.

In a general way, the process can be applied to any linear or branched olefin. It suits particularly well olefins containing 2 to 20 carbon atoms in the molecule such as ethylene, propylene, butenes, pentenes, hexenes, octenes, dodecenes, octadecenes, and so on. These olefins can be used alone or in mixture thereof.

As suitable amines, there may be particularly mentioned secondary aliphatic, aromatic and cycloaliphatic amines. Amines containing 2 to 20 carbon atoms are particularly suitable, such as dimethylamine, diethylamine, dipropylamine, diisopropylamine, dibutylamine, diisobutylamine, dipentylamine, dihexylamine, diheptylamine, dioctylamine, di(ethylhexyl) amine, dinonylamine, diphenylamine, dibenzylamine, butylcyclooctylamine, and so on. These amines can be used alone or in mixture thereof.

The reaction is achieved in the presence of a solvent which can be an alcohol, a saturated or aromatic hydrocarbon, an ether-oxide, alone or in mixture. Reaction temperatures are generally between 60° and 250° C, preferably between 100 and 200° C. Reaction times range from 10 minutes to 10 hours, preferably 30 minutes to 5 hours. Partial pressures of hydrogen and carbon monoxide can vary widely and are preferably each between 10 and 120 bars.

The used catalysts are effective at a low concentration. Thus, concentrations between $5 \times 10^{-6}$ and $5 \times 10^{-3}$ mole of catalyst for each liter of total reaction mixture provide the desired results, this reaction mixture including the solvent and the reactants in volume proportions between 10-90 and 90-10.

The whole reaction conditions and the activity of the catalyst have an effect at once on the transformation of the olefin and on the noted selectivity in substituted amines, such selectivity being defined by the ratio of quantity of produced amines to quantity of consumed olefin, and it can reach 100% without ever being lower than 60%. This is an important advance in relation to the performances of the prior art.

In a general way, the reaction is carried out as follows:

In a vessel fitted with devices for gas injection, agitation and heating, the olefin, solvent, catalyst and amine are successively introduced. Carbon monoxide and hydrogen are then injected under defined partial pressures. The mixture is then heated, under agitation, to the desired temperature. After cooling and degasing of the vessel, the mixture resulting from the reaction is analysed by vapor phase chromatography and the quantity of produced olefin and the quantity of consumed olefin are calculated. The conversion rate of olefin and the selectivity in amine can thus be calculated.

The following examples, given in a non-limitative way, illustrate the invention.

EXAMPLE 1

There is introduced into a vessel 6.7 g of 1-hexene, 10 ml of toluene, 0.1 g of Rh (CO)$_2$Cl (paratoluidine) and 3.6 g of dimethylamine. The contents are heated under agitation at 150° C for 5 hours at a pressure of 60 bars of carbon monoxide and 60 bars of hydrogen. Heptyldimethylamines are obtained with a selectivity of 98% relative to 1-hexene, the conversion rate of 1-hexene being 100%.

EXAMPLE 2

Example 1 is repeated, but under pressures of carbon monoxide and hydrogen respectively of 30 bars and 30 bars. The conversion rate of 1-hexene is still 100%, but the selectivity in amines relative to 1-hexene is only 81%.

EXAMPLE 3

To the vessel are introduced 10 ml of toluene, 6.7 g of hexene, 0.1 g of Rh Cl$_3$[S (C$_2$H$_5$)$_2$]$_3$ and 3.6 g of dimethylamine. It is then heated under agitation at 150° C at 60 bars of carbon monoxide and 60 bars of hydrogen for 5 hours. Heptyldimethylamines are obtained with a selectivity of 97% relative to 1-hexene, the conversion rate of 1-hexene being 100%.

EXAMPLE 4

Example 3 is repeated, but under pressures of carbon monoxide and hydrogen respectively of 30 bars and 30 bars. The conversion rate of hexene is still 100% but selectivity in amines relative to 1-hexene is only 95%.

EXAMPLE 5

Ten ml of ethanol, 6.7 g of 1-hexene, 3.6 g of dimethylamine, and 0.1 g of Rh (CO) Cl [P(OC$_6$H$_5$)$_3$]$_2$ are introduced into a vessel. It is then heated at 140° C under 60 bars of carbon monoxide and 60 bars of hydrogen for 6 hours. Heptyldimethyl-amines are thus obtained with a selectivity of 91% with regard to 1-hexene, the conversion rate of 1-hexene being 89%.

EXAMPLE 6

Ten ml of ethanol, 6.7 g of 1-hexene, 3.6 g of dimethylamine and 0.001 g of

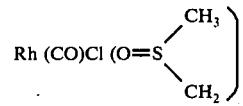

are introduced into a vessel. It is then heated at 200° C under 90 bars of hydrogen and 30 bars of carbon monoxide for 5 hours. Heptyldimethlamines are thus obtained with a selectivity of 83% with regard to 1-hexene, the conversion rate of 1-hexene being 44%.

EXAMPLE 7

Ten ml of ethanol, 6.7 g of 1-hexene, 0.00046 g of Rh (DMGH)$_2$ — DMGH being the dimethylglyoximato anion — and 3.6 g. of dimethylamine are introduced into a vessel. It is then heated at 150° C under 90 bars of hydrogen and 30 bars of carbon monoxide for 5 hours. Heptyldimethylamines are thus obtained with a selectivity of 67% with regard to 1-hexene, the conversion rate being 68%.

EXAMPLE 8

Into a vessel there are introduced 6.7 g of 1-hexene, 3.6 g of dimethylamine and a catalyst constituted by the mixture, extemporaneously prepared, of 1 ml of a toluene solution containing 6 × 10$^{-4}$ g of [Rh(CO)$_2$Cl]$_2$ and of 1 ml of toluene solution containing 5 × 10$^{-4}$ of dimethylsulfoxide. Such a mixture corresponds to about 0.0010 g of $$Rh (CO) Cl(OS\begin{matrix}CH_3\\ \\CH_3\end{matrix})_2.$$

The mixture in 10 ml of toluene is heated at 150° C under 90 bars of hydrogen and 30 bars of carbon monoxide for 5 hours. Heptyldimethylamines are thus obtained with a selectivity of 68% with regard to 1-hexene, the conversion rate of 1-hexene being 96%.

EXAMPLE 9

Into a reactor are introduced 6.7 g of 1-hexene, 3.6 g of dimethylamine, 10 ml of ethanol and 0.141 g of RuCl$_2$[P (OC$_6$H$_5$)$_3$]$_4$. It is then heated at 150° C under 60 bars of hydrogen and 60 bars of carbon monoxide for 5 hours. Heptyldimethylamines are thus obtained with a selectivity of 91% relative to 1-hexene, the conversion rate of 1-hexene being 89%.

EXAMPLE 10

Into a reactor are introduced 6.7 g of 1-hexene, 3.6 g of dimethylamine, 10 ml of ethanol, and 0.38 g of Ru Cl$_2$(CO)$_2$(pyridine)$_2$. It is then heated at 160° C under 60 bars of hydrogen and 60 bars of carbon monoxide for 4 hours 30 minutes. Heptyldimethylamines are thus obtained with a selectivity of 77% with regard to 1-hexene, the conversion rate of the 1-hexene being 29%.

EXAMPLE 11

Into a reactor are introduced 6.7 g of 1-hexene, 3.6 g of dimethylamine, 10 ml of ethanol and 0.039 g of RuCl$_2$(CO)$_2$ (bipyridine). It is then heated at 150° C under 60 bars of hydrogen and 60 bars of carbon monoxide for 5 hours. Heptyldimethylamines are thus obtained with a selectivity of 68% with regard to 1-hexene the conversion rate of the 1-hexene being 23%.

EXAMPLE 12

A complex is prepared by bubbling carbon monoxide in a boiling ethanol solution of Ru Cl, 3 H$_2$O according to the method described by Stephensen et al. (J. Inorganic Nuclear Chemistry (1966) — 28-951). This solution contains 0.407 g of ruthenium in 50 ml. To 12.5 ml of this solution, there is added 0.21 ml of dimethylsulfoxide and an aliquot fraction of the resulting solution which contains 0.1 milliatom.g of Ru in the form of the complex, is used as a catalyst. The above-defined catalyst, 6.7 g of 1-hexene and 3.6 g of dimethylamine are introduced into a reactor, and the reaction is carried on in ethanol at 150° C for 5 hours, under 90 bars of hydrogen and 30 bars of carbon monoxide. Heptyldimethylamines are thus obtained with a selectivity of 84% with regard to hexene, the conversion of the 1-hexene being 60%.

EXAMPLE 13

To 6.7 g of 1-hexene there are added in a reactor 3.6 g of dimethylamine, 10 ml of ethanol and 0.1414g of Pt [P(OC$_6$H$_5$)$_3$]$_4$. It is then heated at 200° C under 60 bars of hydrogen and 60 bars of carbon monoxide for 5 hours. Heptyldimethylamines are thus obtained with a selectivity of 61% with regard to 1-hexene, the conversion rate of 1-hexene being 12%.

EXAMPLE 14

There are introduced 6.7 g of 1-hexene, 3.6 g of dimethylamine, 10 ml of ethanol and 0.08 g of Pd Cl$_2$ [P (OC$_6$H$_5$)$_3$]$_2$ into a reactor. It is then heated to 150° C under 60 bars of hydrogen and 60 bars of carbon monoxide for 5 hours. Heptyldimethylamines are thus obtained with a selectivity of 62% with regard to 1-hexene, the conversion rate of 1-hexene being 38%.

EXAMPLE 15

An ethanol solution of 1-butene, containing 4.5 g of 1-butene and 10 ml of ethanol is introduced into a reactor; 3.6 g of dimethylamine and 0.1 g of

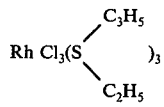

are added. It is then heated under agitation at 150° C for 30 minutes, under 60 bars of hydrogen and 60 bars of carbon monoxide. Amyldimethylamines are thus obtained with a yield of 97% with regard to 1-butene.

EXAMPLE 16

Example 15 is repeated, but 1-butene is replaced by 13.5 g of 1-dodecene. Tridecyldimethylamines are thus obtained with a selectivity of 98% with regard to 1-dodecene, the conversion rate of 1-dodecene being 100%.

EXAMPLE 17

20.2 g of 1-octadecene, 10 ml of ethanol, 3.6 g of dimethylamine and 0.1 g of Rh (CO)Cl [P(OC$_6$H$_5$)$_3$]$_2$ are introduced into a reactor. It is then heated at 200° C for 3 hours under 60 bars of carbon monoxide and 60 bars of hydrogen. Nonadecyldimethylamines are thus obtained with a selectivity of 97% with regard to 1-octadecene, transformation rate of the 1-octadecene being 98%.

EXAMPLE 18

There are introduced 6.7 g of 1-hexene, 10 ml of ethanol, 10.3 g of dibutylamine and 0.1 g of Rh (CO)$_2$Cl (paratoluidine) into a reactor. It is heated at 150° C for 1 hour under 60 bars of carbon monoxide and 60 bars of hydrogen. Heptyldibutylamines are thus obtained with a selectivity of 98% with regard to 1-hexene, the transformation rate of the 1-hexene being 100%.

EXAMPLE 19

There are introduced into a reactor 6.7 g of 1-hexene, 10 ml of ethanol, 6.8 g of piperidine and 0.1 g of Rh CO Cl [P (OC$_6$H$_5$)$_3$]$_2$. It is heated at 150° C for 3 hours under 60 bars of carbon monoxide and 60 bars of hydrogen. Heptylpiperidines are thus obtained with a selectivity of 98% with regard to 1-hexene, the transformation rate the hexene being 97%.

It will be obvious to those skilled in the art that various changes may be made without departing from the scope of the invention and the invention is not to be considered limited to what is described in this specification.

We claim:

1. A process for the manufacture of a substituted amine comprising:
   reacting at least one olefin, carbon monoxide, hydrogen and at least one secondary amine, under partial pressures of hydrogen and carbon monoxide from 10 to 120 bars, at a temperature from 60° to 250° C for a reaction time from 10 minutes to 10 hours,
   in the presence of a catalyst constituted by a coordination complex of a metal of Group VIII containing at least one of the following ligands: aliphatic, aromatic, arylaliphatic phosphites, hexamethylphosphorotriamide, aliphatic and cyclic ethers, primary, secondary and tertiary amines, heterocyclic bases, disulphides, heterocycles containing sulfur or ligands including several donor atoms containing sulfur and oxygen, oxygen and nitrogen, or sulfur and nitrogen;
   wherein the chain added to said secondary amine has one more carbon atom than said olefin.

2. Process according to claim 1, wherein the olefin is a linear or branched olefin containing 2 to 20 carbon atoms.

3. Process according to claim 1, wherein reaction temperature is between 100 and 200° C.

4. Process according to claim 1, wherein said coordination complex is formed in situ in the reaction mixture.

5. Process according to claim 1, wherein the reacted amines are secondary aliphatic, aromatic, or cycloaliphatic amines containing 2 to 20 carbon atoms.

6. Process according to claim 1, wherein said coordination complex is used in proportions between 5 × 10$^{-6}$ and 5 × 10$^{-3}$ mole/gram by liter of total reaction mixture.

7. A process according to claim 1 wherein said Group VIII metal is palladium, platinum, ruthenium, or rhodium.

8. A process in accordance with claim 1 wherein said catalyst is selected from the group consisting of Rh (CO)$_2$ Cl (paratoluidine), Rh Cl$_3$ [S (C$_2$H$_5$)$_2$]$_3$, Rh (CO) Cl [P(OC$_6$H$_5$)$_3$]$_2$, Rh (CO) Cl [O=S(CH$_3$)$_2$]$_2$, Rh(dimethylglyoximate)$_2$ and Ru Cl$_2$ [P(OC$_6$H$_5$)$_3$]$_4$.

* * * * *